United States Patent
Katcha et al.

(10) Patent No.: US 7,522,705 B2
(45) Date of Patent: Apr. 21, 2009

(54) POWER HANDLING METHODS AND APPARATUS

(75) Inventors: Jason Stuart Katcha, Whitefish Bay, WI (US); Jonathan Richard Schmidt, Wales, WI (US)

(73) Assignee: General Electric Company, Schenectady, NY (US)

( * ) Notice: Subject to any disclaimer, the term of this patent is extended or adjusted under 35 U.S.C. 154(b) by 3 days.

(21) Appl. No.: 11/559,877

(22) Filed: Nov. 14, 2006

(65) Prior Publication Data

US 2008/0112537 A1 May 15, 2008

(51) Int. Cl.
*H05G 1/24* (2006.01)

(52) U.S. Cl. .............................. 378/103; 378/4; 378/102

(58) Field of Classification Search ...................... 378/4, 378/101–118
See application file for complete search history.

(56) References Cited

U.S. PATENT DOCUMENTS

| | | | | |
|---|---|---|---|---|
| 4,053,778 A | 10/1977 | Franke | ........................ | 250/402 |
| 4,079,265 A | 3/1978 | Woodburn | .................. | 307/108 |
| 4,080,558 A | 3/1978 | Sullivan | ....................... | 320/39 |
| 4,186,329 A | 1/1980 | Fairbairn | ..................... | 315/241 |
| 4,321,523 A | 3/1982 | Hammel | ....................... | 320/14 |
| 5,017,800 A | 5/1991 | Divan | .......................... | 307/66 |
| 5,036,284 A | 7/1991 | Cichanski | ................... | 324/433 |
| 5,646,835 A | 7/1997 | Katcha | ......................... | 363/98 |
| 6,118,845 A | 9/2000 | Simon et al. | .................. | 378/62 |
| 6,351,401 B1 * | 2/2002 | Scheel et al. | .................. | 363/98 |
| 6,370,224 B1 | 4/2002 | Simon et al. | .................. | 378/62 |
| 6,470,207 B1 | 10/2002 | Simon et al. | ................ | 600/426 |
| 6,477,400 B1 | 11/2002 | Barrick | ........................ | 600/426 |
| 6,892,090 B2 | 5/2005 | Verard et al. | ................ | 600/424 |
| 6,920,347 B2 | 7/2005 | Simon et al. | ................ | 600/424 |
| 6,947,786 B2 | 9/2005 | Simon et al. | ................ | 600/427 |
| 6,968,224 B2 | 11/2005 | Kessman et al. | ............ | 600/407 |
| 2005/0281377 A1 | 12/2005 | Heinze | ....................... | 378/101 |
| 2006/0210013 A1 * | 9/2006 | Kasuya | .......................... | 378/4 |
| 2007/0158118 A1 * | 7/2007 | King | .......................... | 180/65.1 |

OTHER PUBLICATIONS

U.S. Appl. No. 11/412,590, filed Apr. 27, 2006; Titled: Methods and Apparatus for Mobile Imaging Systems; First Named Inventor: Richard Larry Anderton.

* cited by examiner

*Primary Examiner*—Jurie Yun
(74) *Attorney, Agent, or Firm*—Fisher Patent Group, LLC; Thomas M. Fisher

(57) ABSTRACT

Apparatus includes a fixed computed tomography (CT) system including a storage device configured to share power delivery with an input power line in order to reduce peak load requirements of the input power line.

7 Claims, 5 Drawing Sheets

CT System with Stored Energy and Boost Inverter

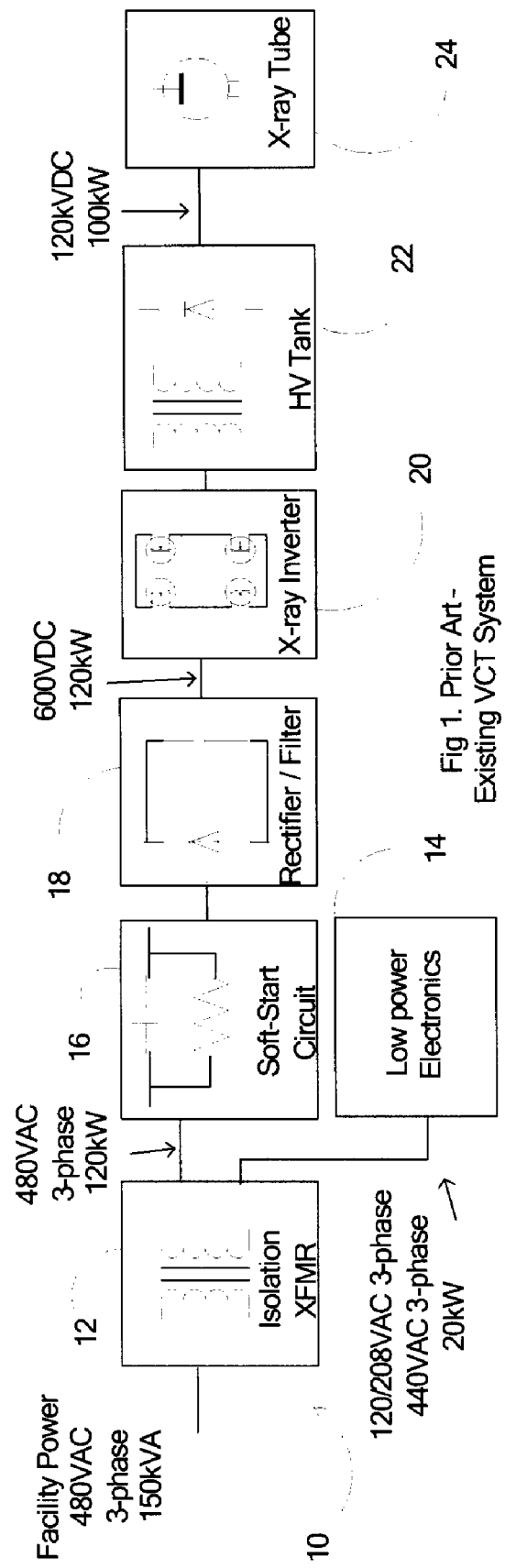
Fig 1. Prior Art - Existing VCT System

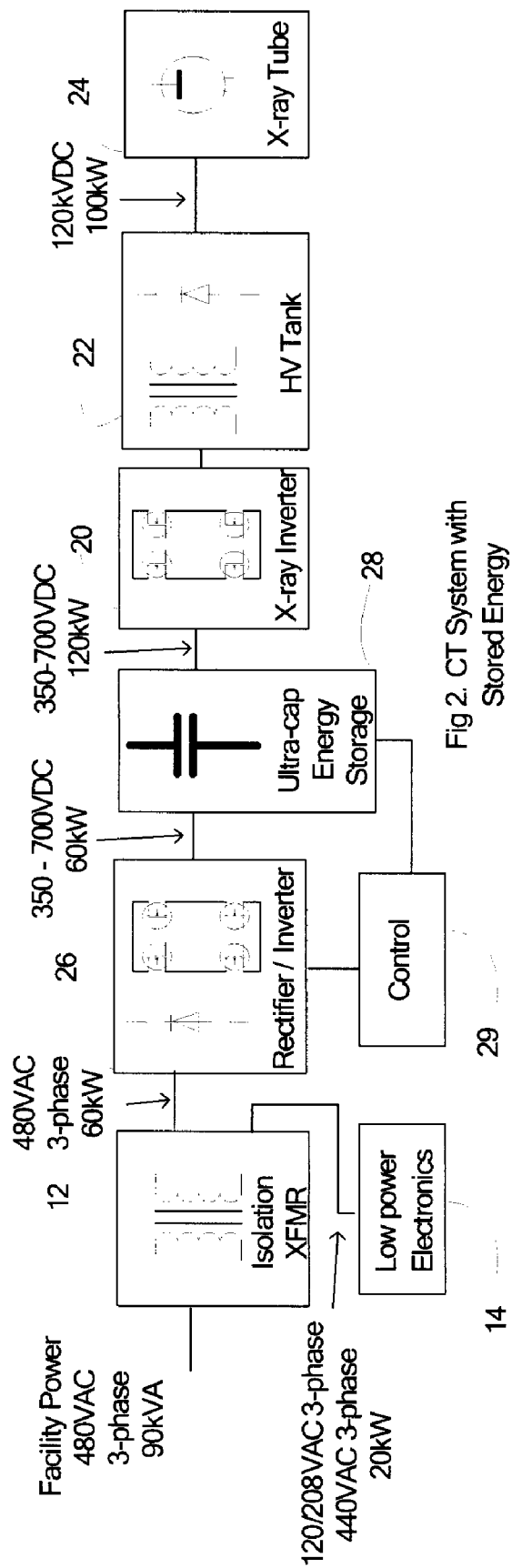
Fig 2. CT System with Stored Energy

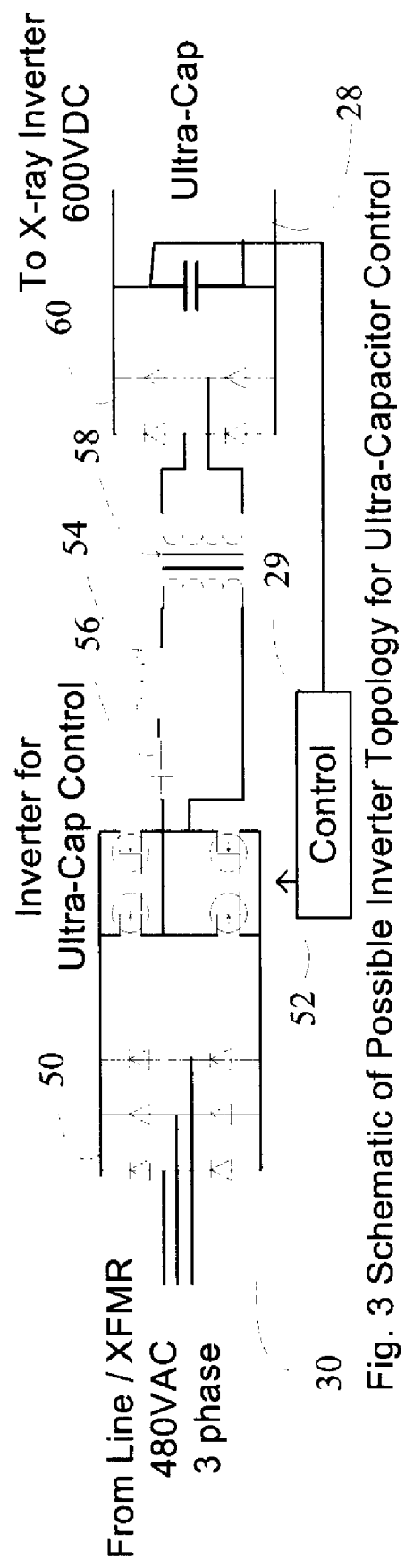
Fig. 3 Schematic of Possible Inverter Topology for Ultra-Capacitor Control

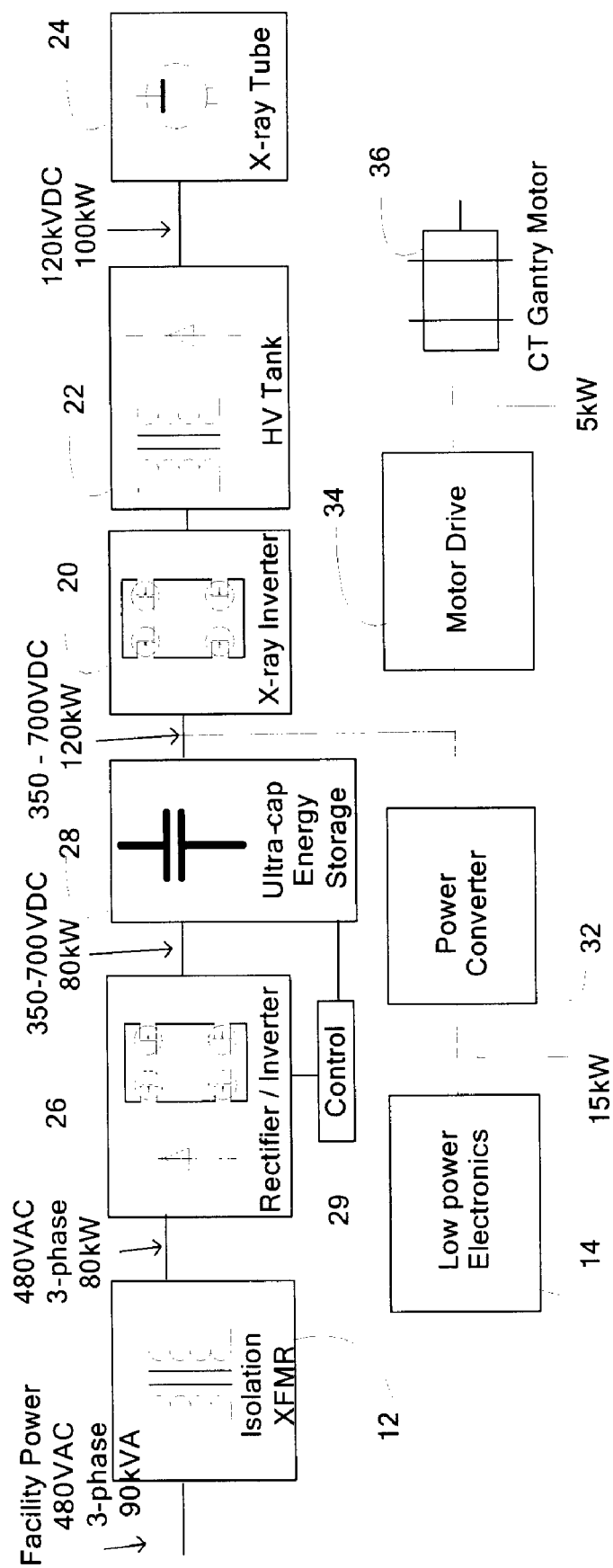
Fig 4. CT System with Stored Energy, UPS Function, and Gantry Energy Recovery

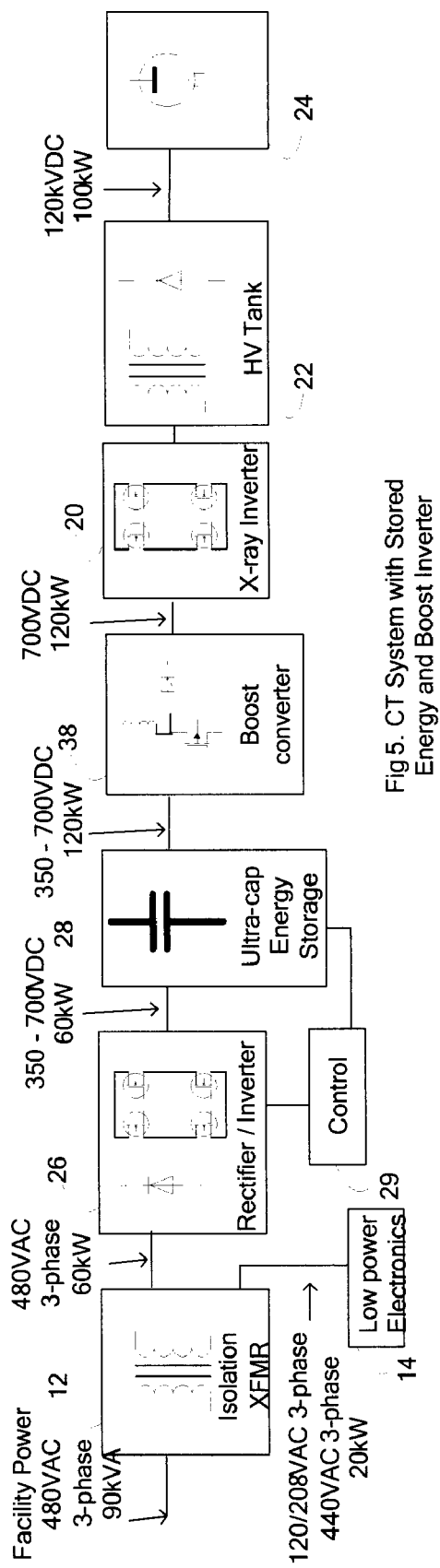
Fig 5. CT System with Stored Energy and Boost Inverter

POWER HANDLING METHODS AND APPARATUS

BACKGROUND OF THE INVENTION

This invention relates generally to diagnostic imaging methods and apparatus, and more particularly, to methods and apparatus that provide for the handling of computed tomography (CT) power requirements.

Existing CT systems have high input power requirements that drive high installation costs for purchasers of CT systems. This power is primarily required for the x-ray tube, which uses 100 kW peak, but only 4 kW average. Therefore a CT system that is able to deliver high peak power, while only drawing reduced average power from the input line is highly desirable. Described below is a CT system that uses an energy storage device to store energy and reduce peak power required from the input line.

BRIEF DESCRIPTION OF THE INVENTION

In one aspect, apparatus includes a fixed computed tomography (CT) system including a storage device configured to share power delivery with an input power line in order to reduce peak load requirements of the input power line.

In another aspect, apparatus includes a computed tomography (CT) system comprising a storage device configured to share power delivery with an input power line in order to reduce peak load requirements of the input power line, wherein the storage device comprises a plurality of ultra-capacitors.

In still another aspect, a system includes an x-ray source, an x-ray detector positioned to receive x-rays emitted from the source, and an energy storage device operationally coupled to the source, wherein the energy storage device recovers energy when a gantry is slowed down and/or a tube rotor is slowed down.

BRIEF DESCRIPTION OF THE DRAWINGS

FIG. 1 illustrates a known volume computed tomography.

FIG. 2 illustrates one embodiment of using ultra-capacitors to locally store energy in order to reduce peak power required from the facility power line.

FIG. 3 illustrates a schematic of a possible implementation of the inverter topology for the control of the ultra-capacitor.

FIG. 4 shows an alternative embodiment, where the ultra-capacitors can be used to provide a short term back-up power for the auxiliary power loads.

FIG. 5 shows another alternative embodiment, where a boost converter is inserted between the ultra-capacitor and the x-ray inverter.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

One embodiment described here uses an energy storage device to share power delivery capability with the input line during peak tube power demand, thereby reducing facility power requirements. There are numerous methods to locally store energy, including but not limited to: a fly-wheel (mechanical energy), batteries (chemical energy), superconducting magnets (magnetic energy, and capacitors (electro-static energy). Each of these technologies present its own set of advantages and disadvantages. However, recent development of "Ultra-capacitors" has made them (ultra-capacitors) particularly attractive.

So-called "Ultra-capacitors" provide around 20 times the energy storage density compared with other capacitor technologies. They have been developed in the past 10 years, are well known in the power design community and are readily available from multiple suppliers (Maxwell, Nesscap, Panasonic, etc.). For example, a typical, readily available ultra-capacitor has an energy density of over 10,000 Joules/liter vs. less than 500 Joules/liter for a standard electrolytic capacitor. Compared to batteries, ultra-capacitors can deliver higher peak power for a given volume and are specified to provide greater than 1M deep charging cycles. Batteries provide only 1000 to 10,000 charging cycles before wearing out, resulting in battery replacement in less than a year for a CT application in even the most optimistic scenario.

Referring to FIG. 1, today's fixed computed tomography (CT) system 10 requires 150 kVA capable input power. This is coupled to an isolation transformer 12, soft start circuitry 16, a rectifier filter 18, an x-ray high voltage power supply 22, and an x-ray tube 24. Typically, an x-ray inverter 20 is also present as are low-power electronics 14. The isolation transformer 12 also provides around 20 kW of auxiliary power for sub-systems other than X-ray generation (Data Acquisition, Reconstruction computer, Host computer, gantry electronics, etc. collectively the low-power electronics 14). Considering all power required for the CT system (tube, auxiliary loads, plus system inefficiencies), 140 kW peak power is required from the power line. This translates into a "150 kVA" rated facility power requirement, which places a large additional cost on CT purchasers to site the systems. By a "fixed CT system", it is meant to be permanently installed in a building or in a truck. The system is not movable in the manner that a mobile C-arm CT is. In one embodiment, the CT system is a volume CT (VCT) in that it has at least a 32 slice capacity.

FIG. 2 illustrates one embodiment of using ultra-capacitors to locally store energy in order to reduce peak power required from the facility power line. The ultra-capacitors 28 and a control inverter 26 are inserted between the isolation transformer 12 and the x-ray inverter 20. The soft-start circuit 16 shown in FIG. 1, can be eliminated because the control inverter 28 will limit the input power and charge the ultra-capacitor bank 28 at a pre-determined rate. A control circuit 29 may be used to control the rectifier/inverter 26 and/or the ultra-capacitors 28.

The ultra-capacitor bank 28 is sized to provide power long enough such that the facility power line rating can be reduced. For example, if 60 kW is required from the ultra-capacitor for a duration of 5 seconds, this equates to the following amount of energy:

$$K[J] = P[W] \cdot T[s]$$

$$K = 60k[W] \cdot 5[s] = 300k[J]$$

The Capacitance required is then:

$$C[F] = \frac{2K}{V_1^2 - V_2^2} = \frac{2 \cdot 300k[J]}{(700[V])^2 - (350[V])^2} = 1.63[F]$$

Where $V_1$ is the ultra-capacitor initial voltage and $V_2$ is the ultra-capacitor final voltage.

A bank of ultra-capacitors with 1.63 F and capable of 700V peak, has about 40 liters of volume. This could easily be packaged in a small cabinet. The cost of this ultra-capacitor bank for this example is reasonable. Returning to FIG. 2, with the ultra-capacitor bank from this example, the facility power can be reduced from a 150 kVA line to a 90 kVA line. This will provide large savings to the customer, and make possible a VCT mobile configuration wherein the VCT system is in a mobile trailer.

FIG. 3 illustrates a schematic of a possible implementation of the inverter topology 26 for the control of the ultra-capacitor 28. A 3 phase rectifier bridge 50 is coupled to an H-bridge inverter 52, a series resonant inductor 54, a capacitor 56, a high frequency transformer 58, a plurality of rectifiers, 60 and the ultra-capacitor 28. This topology provides complete control of the ultra-capacitor 28 using a series-resonant converter 26, which has the benefits of: the elimination of the soft start circuit 16; with low-loss switching; low electromagnetic (EM) noise, and a high frequency transformer with a reduced size.

FIG. 4 shows an alternative embodiment, where the ultra-capacitors 28 can be used to provide a short term back-up power for the auxiliary power loads. Also shown is the CT gantry motor drive power coming from the ultra-capacitors 28. A power converter 32 is coupled to the ultra-capacitors 28 and provides power to the low power electronics 14. A motor drive 34 is also coupled to the ultra-capacitors 28 and the gantry motor 36. This eliminates the need for a dynamic brake circuit and resistors by allowing the ultra-capacitors 28 to recover the energy when the motor 36 slows the gantry. This energy recovery action will save power (up to 3 kW or around 10% of the CT scanned total power).

FIG. 5 shows another alternative embodiment, where a boost converter 38 is inserted between the ultra-capacitor 28 and the x-ray inverter 20. This allows better usage of the ultra-capacitor energy and would provide less voltage variation to the x-ray inverter's 20 input.

Technical effects include the reduced CT system input power input requirements, allowing less expensive siting costs and possible VCT mobile configuration, and an integrated uninterrupted power supply (UPS) function for additional low cost. Technical effects also include an energy recovery from gantry drive motor lowers average power requirements (up to 10% reduced power consumption), and an energy recovery from a motor in the x-ray tube slowing down. The embodiment with the boost converter 38 provides maximum utilization of the ultra-capacitor energy.

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. Apparatus comprising a fixed computed tomography (CT) system comprising a storage device configured to share power delivery with an input power line in order to reduce peak load requirements of the input power line, and a control operationally coupled to said storage device wherein said storage device is energized by said control by slowing down a gantry and/or slowing down a tube rotor, wherein said storage device comprises a plurality of ultra-capacitors wherein a series resonant converter is configured to control a voltage of the ultra-capacitors and a boost converter is connected to an output of said plurality of ultra-capacitors.

2. Apparatus comprising a computed tomography (CT) system comprising a storage device configured to share power delivery with an input power line in order to reduce peak load requirements of the input power line, wherein the storage device comprises a plurality of ultra-capacitors, and the CT system comprises a control wherein said storage device is energized by said control by slowing down a gantry and/or slowing down a tube rotor, wherein a series resonant converter is configured to control a voltage of the ultra-capacitors and a boost converter is connected to an output of said plurality of ultra-capacitors.

3. Apparatus in accordance with claim 2 wherein said storage device is configured to provide backup power to at least one electronic device within the CT system.

4. Apparatus in accordance with claim 3 further comprising a mobile trailer, said CT system position within said mobile trailer.

5. Apparatus in accordance with claim 2 further comprising a mobile trailer, said CT system position within said mobile trailer.

6. A system comprising:
an x-ray source;
an x-ray detector positioned to receive x-rays emitted from said source;
a control operationally coupled to said source; and
an energy storage device operationally coupled to said source and said control, said energy storage device recovers energy using said control when a gantry is slowed down and/or a tube rotor is slowed downs, wherein said storage device comprises a plurality of ultra-capacitors wherein a series resonant converter is configured to control a voltage of the ultra-capacitors and a boost converter is connected to an output of said plurality of ultra-capacitors.

7. A system in accordance with claim 6 wherein said system is configured to be operable within a mobile trailer.

* * * * *